April 11, 1972 S. McGREDY IV Plant Pat. 3,111
ROSE PLANT
Filed Dec. 18, 1969
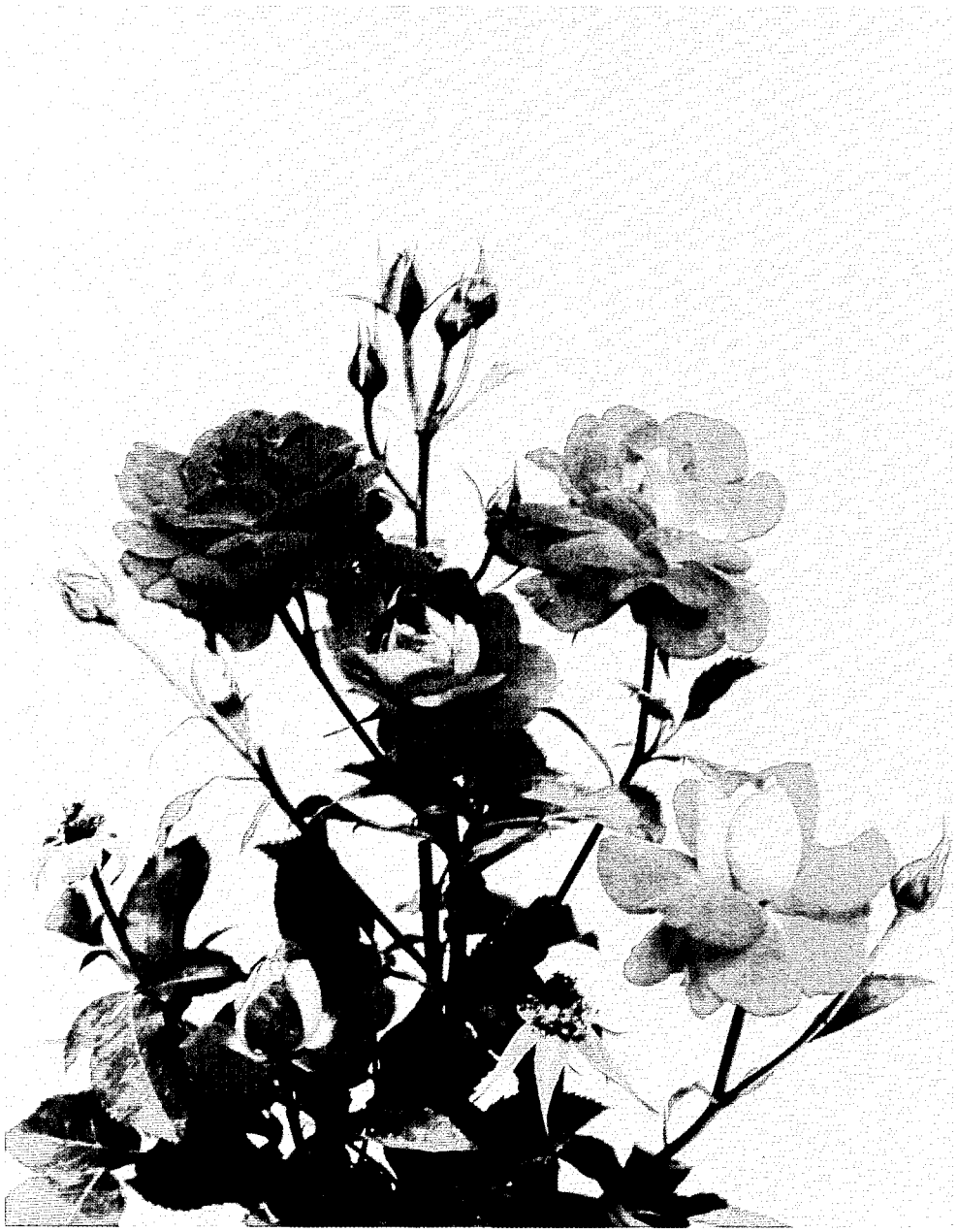

United States Patent Office

Plant Pat. 3,111

Patented Apr. 11, 1972

3,111

ROSE PLANT

Samuel McGredy IV, Portadown, Ireland, assignor to Armstrong Nurseries, Inc., Ontario, Calif.

Filed Dec. 18, 1969, Ser. No. 886,430

Int. Cl. A01h *5/00*

U.S. Cl. Plt.—22 1 Claim

ABSTRACT OF THE DISCLOSURE

A bush rose plant of the floribunda class adapted for outdoor cultivation, and being of rather stiff upright habit, with erect and almost smooth peduncles. The buds are characterized by gland-tipped cilia on the surface of the bud and by frequent foliaceous parts extending beyond the tip of the bud before the calyx breaks. The flowers are usually borne in irregular clusters on strong medium length stems, being of small to average diameter for its class, from 3″ to 3¾″, with 25 to 28 petals, and 2 or 3 petaloids. The color is at first relatively pale pink, with strong purplish red overlay at the outer margins of the petals, the inner surfaces being predominantly bright red in color. When fully open, the center of the bloom shows nearly white around the flower stamens.

This invention relates to a new variety of floribunda bush rose, well adapted for outdoor cultivation, for cut flowers and garden decoration. The seed parent of this new variety was an unnamed seedling which was derived by crossing Mme. Leon Cuny×Columbine, the pollen parent being the Paddy McGredy rose, P.P. No. 2,327.

The plant holds its distinguishing characteristics through succeeding propagations by budding.

Although the new variety was originally propagated in Portadown, County Armagh, Northern Ireland, the description which here follows was made from a plant budded and grown in Ontario, Calif., from the Irish stock.

The seed parent of this new variety was not introduced to the public nor named. It has since been lost, but it was produced from a cross of Mme. Leon Cuny×Columbine. One of the outstanding characteristics of Mme. Leon Cuny was its very large double bloom. The flower of this new variety is neither very large nor very double. Mme. Leon Cuny was fragrant, whereas this new variety has little, if any, fragrance. Columbine also is described as very fragrant, and has a creamy-yellow flower tinged with pink. The new variety is neither very fragrant nor does it have more than a hint of yellow at the base of the petals.

The new variety may be distinguished from its pollen parent, Paddy McGredy, in the following ways: Paddy McGredy is described as having a large flower, 4″ in diameter, whereas the blooms of the new variety are small to average for the class, ranging from 3″ to 3¾″ in diameter. Paddy McGredy presents 30 to 35 petals in the bloom, whereas the new variety has 25 to 28 petals, plus 2 or 3 petaloids. Paddy McGredy is described as having a deep rose-pink flower, whereas the bloom of the new variety is a bicolor, with a near white, or very pale pink reverse, and a bright purplish-pink overlaid with dark red on the inner surfaces of the petals.

The accompanying drawing illustrates the plant in color, and shows the flowering thereof from bud to full bloom.

In the disclosure which follows, the color values are based on the Nickerson Color Fan, except where the popular color designation is sufficiently descriptive for present purposes.

The flowers of the new variety are usually borne several to the stem, in irregular rounded clusters, on strong medium length stems, although the flowers are also sometimes borne singly. The new variety is free blooming, outdoors, and blooms intermittently during the growing season. The fragrance is slight.

*Bud*

As to the bud: the peduncle is of average length and average caliper, being erect, almost smooth, but having some gland-tipped cilia and a few hairs. The color is Moderate Yellow Green, 2.5GY5/5, overlaid with Moderate Reddish Brown, 10R¾.

Before the calyx breaks, the buds are of small size, ovoid in form, and of medium length. They have foliaceous appendages, gland-tipped cilia on the surface of the bud, usually with slender much cut foliaceous parts extending beyond the tip of the bud for a distance equal to one-quarter or more of the length of the bud.

As the calyx breaks, the color is Strong Purplish Red, 10RP4/12, overlaid with patches of Dark Red, 2.5R3/7, where first exposed to the sun. The inner surfaces of the sepals have a fine, wooly tomentum.

As the first petal opens, the bud is of average size, ovoid in form and medium length, and its color on the outside is between Deep Purplish Pink, 5RP6/10, and Strong Purplish Red, 7.5/12, with a small area at the base which is nearly white. The color inside is Moderate Purplish Red, 5RP5/10, overlaid with a color which is between Moderate Red, 2.5R4/10, and Deep Purplish Red, 10RP3/10. There is a medium sized area at the base which is nearly white.

The bud opens up well and it is not retarded or prevented from opening by cold, hot, wet, or dry weather.

*Bloom*

When fully open, the bloom is between small and average size for the class, namely, between about 3″ and 3¾″. The petalage is double, ranging from 25 to 28 petals, plus 2 or 3 petaloids regularly arranged. The form of the bloom is cupped to globular at first, becoming high centered to globular later. The petals at first are loosely cupped with their tips rolled inward, but later, at maturity, they become flat, with their tips rolled outward.

*Petals*

The petals are of medium leathery texture, with inside slightly satiny and the outside slightly shiny. The shape of the outer petals is broadly obovate, scalloped, the apex usually having 1 or 2 notches. The intermediate petals are obovate and scalloped, with apex rounded, and with 1 to 3 notches. The inside petals are nearly round, with apex rounded. The colors may be modified by being washed or tinted with other colors.

The following description is of a newly-opened flower grown outdoors in the month of May, in Ontario, Calif.:

The color of the outside petal, on its outer surface, is near Deep Purplish Pink, 5RP6/10, with the medium sized area at the base nearly white. The inside surface of the outer petal is Moderate Purplish Red, 5RP5/10, overlaid with a color which is between Moderate Red, 2.5R4/10, and Deep Purplish Red, 10RP3/10. The medium sized area at the base is nearly white.

The intermediate petal has an outer surface which is near Very Pale Purple, 7.5P8/5, lightening to Very Pale Purple, 7.5P9/2, at the base. The inner surface of the intermediate petal is Moderate Purplish Pink, 2.5RP7/8, overlaid with a color between Moderate Red, 2.5R4/10, and Dark Red, 5R3/7. A small area at the base is nearly white, enlarging to a moderate area of Deep Purplish Pink, 5RP6/10.

The outer surface of the inner petal has a small area at the base which is nearly white. The remainder darkens gradually, progressing towards the apex until it reaches Light Purplish Pink, 2.5RP8/5. The inside surface of the inner petal is Strong Purplish Red, 7.5RP5/12, overlaid with a color which is between Strong Purplish Red, 10RP4/12, and Deep Purplish Red, 10RP3/10.

The following description is of a flower that had been open for three days outdoors during the month of May, in Ontario, Calif.:

The color of the outside petal, on its outer surface, was Pale Purplish Pink, 10P8/5, with patches of near Deep Purplish Pink, 5RP6/10, where exposed to the sun. A small area at the base was nearly white. The inner surface of the outside petal has a small area at the base which is nearly white but changes abruptly to near Deep Purplish Pink, 2.5RP6/10, for about one-half the length of the petal, and is then gradually overlaid with Deep Purplish Red, 10RP3/10.

The outer surface of the inside petal is near Deep Purplish Pink, 5RP6/10, with the medium sized area at the base nearly white. The inner surface of the inside petal is Deep Purplish Pink, 2.5RP6/10, overlaid with near Deep Purplish Red, 10RP3/10.

The general color effect of the newly-opened flower is a Moderate Purplish Pink, 2.5RP7/8, overlaid with Dark Red, 5R3/7, and with reverse of center petals quite pronounced Light Purplish Pink, 2.5RP8/5.

After the bloom has been three days open, the general color effect is of a Deep Purplish Pink, 2.5RP6/10, overlaid with near Deep Purplish Red, 10RP3/10. When fully open, the center shows nearly white around the flower's stamens.

The petals drop off cleanly. The blooms on the bush in the garden will last for five days in the month of May, in Ontario, Calif. Cut roses grown outdoors and kept at livingroom temperatures will last about four days at the same time and place.

*Reproductive organs*

Stamens: Few to average in number, regularly arranged about the pistils.
Filaments: Short, most with anthers.
Anthers: Small; all open approximately at once.
Pollen: Moderate to abundant, the color of straw.
Pistils: Few to average in number, in the neighborhood of 25 to 30.
Styles: Uneven, short to average length, average caliper, and bunched. Color: near Strong Red, 2.5R5/12.
Stigma: Color not significant.
Ovaries: All protruding from the calyx.
Hips: No hips observed; rarely sets hips at Ontario, Calif.
Sepals: Permanent, moderately long and straight; not significantly colored, either inside or outside.
Seeds: None observed.

*Foliage*

The compound leaves are usually composed of five leaflets. They are of normal quantity, moderately large, heavy, leathery, and glossy. The leaflets are from avoid to lanceolate in shape, with apex often acuminate, round base, and margin doubly serrate.

The upper surface of the nature leaf is between Moderate Olive Green, 5GY4/3, and Grayish Olive Green, 5QY3/2. The undersurface is Moderate Olive Green, 5GY4/3, overlaid with fine grayish hairs between the veins.

The color of the younger leaves, on their upper surface, is near Deep Purplish Red, 7.5RP/39, as an overlay on near Strong Yellow Green, 5GY6/8. The under surface as the young leaves unfold displays a base color near Strong Yellow Green, 5GY6/8, but heavily overlaid with a color between Deep Purplish Red, 10RP3/10, and Deep Purplish Red, 7.5RP3/9.

The rachis is of average to heavy size, smooth on its upper side, but with occasional stipitate glands on the edges. On the underside, it is sparsely prickly, and with some glandular bloom.

The stipules are moderately short, medium-width, with short points, turning out at an angle of about 45°.

The foliage is more resistant than average to mildew, when compared to a large number of other varieties grown under comparable conditions outdoors at Ontario, Calif.

*Growth*

The plant is of bushy upright habit, much branched and vigorous in growth. The canes are of moderately heavy caliper. The cane stems are of a normal green color, and the large prickles which they carry are several in number, of medium-length, slightly hooked downward, with medium-length broad base. Their color is light brown. Small prickles on the main steam are very few. They also are light brown in color. There are no hairs.

The branches are medium green in color, and the large prickles which they carry are several in number, of medium-length, hooked slightly downward, with medium-length broad base. They are light brown in color. The small prickles carried on the branches are very few in number and light brown in color. There are no hairs.

The new shoots are of a purple color, shown in the young leaves, changing rather quickly to the green of the new fully developed leaves. The large prickles on the new shoots are few in number, short to medium-length, hooked slightly downward, with medium-length moderately broad base. Their color is reddish purple. Small prickles on the new shoots are few in number and reddish purple in color. There are no hairs.

I claim:

1. A floribunda bush rose substantially as shown and described herein, and distinguished by novel combinations of features including its rather stiff, upright habit of growth, well adapted for outdoor cultivation, the almost smooth peduncles supporting buds which carry gland-tipped cilia, foliaceous appendages, and much cut foliaceous parts extending beyond the tip of the bud, all on the calyx, which, on opening, yields a flower of small to average size for the class, the bloom usually comprising from about 25 to about 28 petals, with two or three petaloids, the petals being predominantly of bicolored coloration, pale pink on their outer surfaces and red on their inner surfaces.

No references cited.

ROBERT E. BAGWILL, Primary Examiner

UNITED STATES PATENT OFFICE
CERTIFICATE OF CORRECTION

Patent No. PP 3111 Dated April 11, 1972

Inventor(s) Samuel McGredy IV

It is certified that error appears in the above-identified patent and that said Letters Patent are hereby corrected as shown below:

Column 2, line 24 - "7.5/12" should be --7.5RP5/12--

Column 3, line 57 - "avoid" should be --ovoid--

Column 3, line 61 - "nature" should be --mature--

Column 4, line 1 - "5QY3/2" should be --5GY3/2--

Column 4, line 5 - "7.5RP/39" should be --7.5RP3/9--

Column 4, line 29 - "steam" should be --stem--

Signed and sealed this 26th day of September 1972

(SEAL)
Attest:

EDWARD M.FLETCHER,JR.
Attesting Officer

ROBERT GOTTSCHALK
Commissioner of Patents

USCOMM-DC 60376-P69
☆ U.S. GOVERNMENT PRINTING OFFICE : 1969 O—366-334